United States Patent

Shamshoum et al.

Patent Number: 5,387,732
Date of Patent: Feb. 7, 1995

[54] START-UP PROCESS FOR IMPROVED SELECTIVITY IN TOLUENE DISPROPORTIONATION

[75] Inventors: Edwar S. Shamshoum; Ashim K. Ghosh, both of Houston; Thomas R. Schuler, Galena Park, all of Tex.

[73] Assignee: Fina Technology, Inc., Dallas, Tex.

[21] Appl. No.: 40,764

[22] Filed: Mar. 31, 1993

Related U.S. Application Data

[63] Continuation-in-part of Ser. No. 776,937, Oct. 15, 1991, abandoned.

[51] Int. Cl.$^6$ .............................. C07C 3/62
[52] U.S. Cl. ................................ 585/475
[58] Field of Search ....................... 585/475

[56] References Cited

U.S. PATENT DOCUMENTS

| | | | |
|---|---|---|---|
| 3,667,973 | 7/1972 | Mitshe et al. | 502/70 |
| 3,780,122 | 12/1973 | Pollitzer et al. | 585/474 |
| 4,665,258 | 5/1987 | Butler et al. | 585/475 |

Primary Examiner—Asok Pal
Assistant Examiner—P. Achutamurthy
Attorney, Agent, or Firm—Betty M. Ellsworth; M. Norwood Cheairs

[57] ABSTRACT

A process is provided for the disproportionation of a toluene feed stock that includes using an unconventionally low hydrogen to toluene mole ratio during reaction start-up, i.e., until the production of non-aromatics begins to stabilize; thereafter the ratio is increased. Reducing the hydrogen content at the beginning of the reaction substantially lessens any hydrogenation activity, thereby gaining optimum selectivities to benzene at a much sooner rate than that achieved using more conventional hydrogen to toluene ratios. The post start-up increase in hydrogen concentration following stabilized production of non-aromatics is generally believed to enhance the aging character of the catalyst, thereby preserving catalyst life. In practicing the invention, a reaction zone is established loading a metal-modified mordenite catalyst into the reaction zone. A toluene containing feed stock is continuously supplied to the reaction zone. Contemporaneous with the introduction of the toluene, hydrogen gas is introduced into the reaction zone to provide a hydrogen to toluene mole ratio of between 0.5 and 1.5. The feed stock contacts the catalyst forming a disproportionation product containing benzene, xylene(s) and non-aromatic by-products. The disproportionation product is continuously withdrawn and measured to determine its non-aromatic content. When the non-aromatic content of the disproportionation product stabilizes, the amount of hydrogen supplied to the reaction zone is increased.

12 Claims, 4 Drawing Sheets

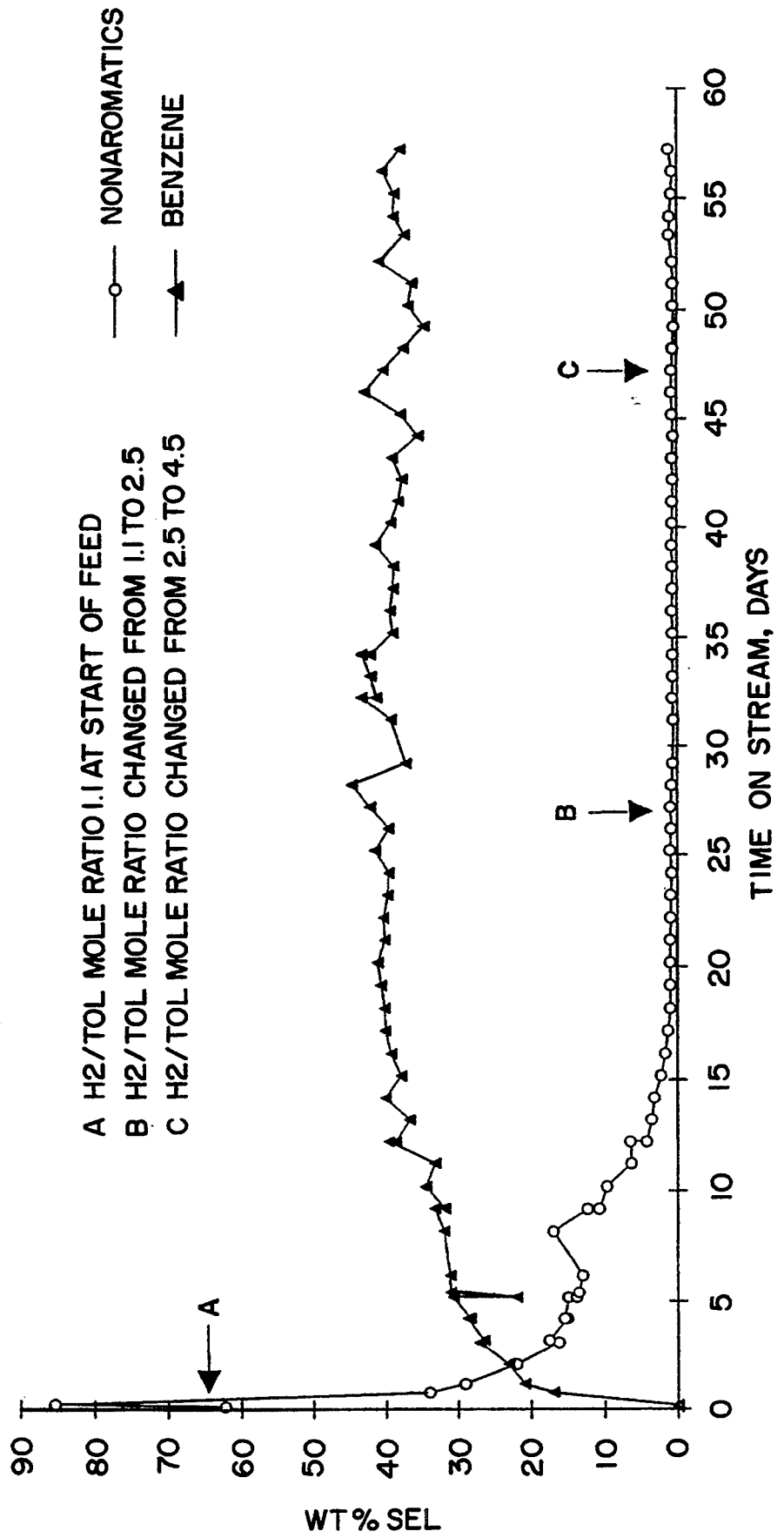

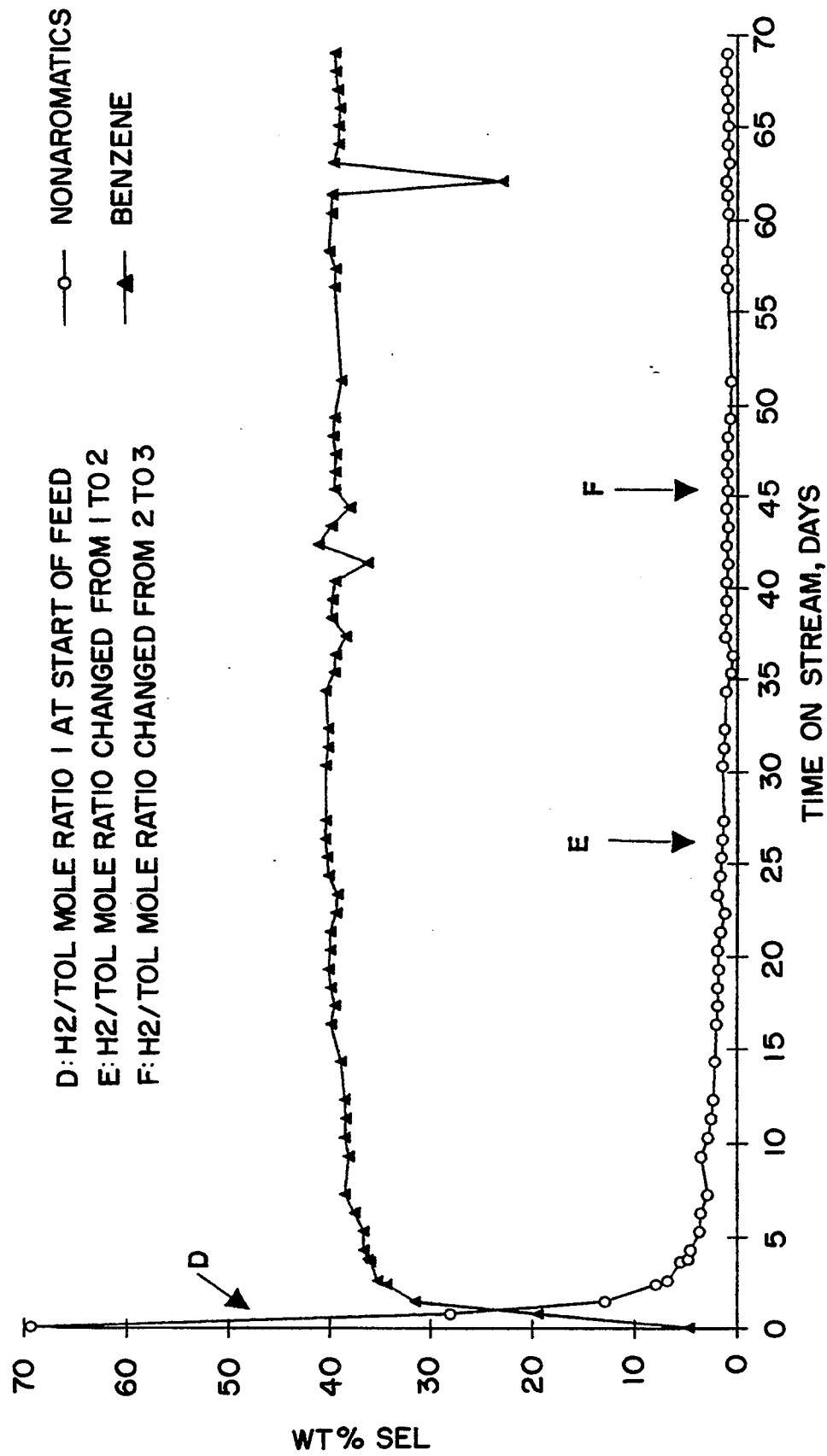

START-UP PROCESS FOR IMPROVED SELECTIVITY IN TOLUENE DISPROPORTIONATION

CROSS REFERENCE TO RELATED APPLICATIONS

This is a continuation-in-part of application Ser. No. 07/776,937, filed Oct. 15, 1991, now abandoned.

FIELD OF THE INVENTION

This invention relates to a start-up procedure for use in the disproportionation of alkylaromatic feedstreams and, more particularly, in the disproportionation of toluene containing feedstocks employing mordenite catalysts of relatively high aluminum content.

DESCRIPTION OF THE RELATED ART

The disproportionation of toluene involves a well known transalkylation reaction in which toluene is converted to benzene and xylene in accordance with the following reaction:

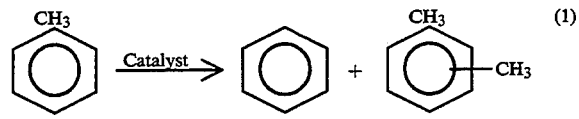

(1)

Reaction (1) is mildly exothermic.

Mordenite is one of a number of molecular sieve catalysts useful in the transalkylation of alkylaromatic compounds. As a crystalline aluminosilicate zeolite, mordenite exhibits a network of silicon and aluminum atoms interlinked by oxygen atoms within the crystalline structure. For a general description of mordenite catalysts, reference is made to Kirk-Othmer, Encyclopedia of Chemical Technology, 3rd Edition, 1981, under the heading "Molecular Sieves", Vol 15 pages 638-643. Mordenite as found in nature or as synthesized to replicate the naturally occurring zeolite, typically exhibits a relatively low silica to alumina mole ratio of about 10 or less. Also known, however, are mordenite catalysts exhibiting a substantially lower alumina content. These aluminum deficient mordenite catalysts exhibit silica to alumina ratios greater than 10, ranging up to about 100, and may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies, et. al. Both the typical and the aluminum deficient mordenites are known to be useful in the disproportionation of toluene.

Disproportionation of toluene feedstock may be performed at temperatures ranging from about 200° C. to about 600° C. or above and at pressures ranging from atmospheric to perhaps 100 atmospheres or above. The specific catalyst, however, may impose constraints on reaction temperatures thus affecting catalyst activity and aging character. In general, the prior art suggests the use of relatively high temperatures when employing the high aluminum mordenites (low silica to alumina ratios) and somewhat lower temperatures when employing the low alumina mordenites. Accordingly, where mordenite catalysts exhibiting high silica/alumina ratios have been employed in the transalkylation of alkylaromatics, it has been the practice to operate toward the lower end of the temperature range.

U.S. Pat. No. 4,665,258 to Butler, et. al., however, discloses disproportionation of a toluene containing feedstock employing an aluminum deficient mordenite catalyst under relatively severe disproportionation conditions; involving a temperature range of 370°-500° C. The mordenite catalysts exhibit silica/alumina mole ratios of at least 30 and, more desirably, within the range of 40-60. The feedstock may be supplied to the reaction zone containing the mordenite catalyst at rates providing relatively high space velocities. The toluene weight hourly space velocity (WHSV) may be greater than 1. Hydrogen is supplied to the reaction zone at a hydrogen/toluene mole ratio within the range of 3-6. The hydrogen pressure may be 500 psi or more. Butler '258 also discloses passing a hot preflush gas, nitrogen or hydrogen, to the reaction zone prior to initiating the disproportionation reaction. The preflush gas is heated to a temperature efficient to substantially dehydrate the catalyst by the time the toluene feed is started. This measure enables the disproportionation process to initially be performed at a somewhat lower temperature and without reduction in toluene conversion. As the disproportionation proceeds, temperature progressively increases to maintain toluene conversion at the desired level, typically about 80 percent of theoretical.

U.S. Pat. No. 4,723,049 to Menard et al. discloses toluene disproportionation carried out over aluminum deficient mordenite of the type disclosed in the aforementioned patent to Butler '258. Menard discloses a reaction zone temperature of 370°-500° C. with an unmodified aluminum deficient mordenite catalyst. During the process, the supply of toluene to the reaction zone is interrupted while the supply of hydrogen is continued. Preferably the period of interruption during which hydrogen supply is continued is for at least one day prior to reinstating the supply of toluene feedstock to the reaction zone. This mode of operation is disclosed to enhance the aging quality of the catalyst and show a reduction in reactor zone temperature without a corresponding decrease in toluene conversion.

It is also a common practice to promote an aluminum deficient mordenite catalyst with a catalytically active metallic content. For example, U.S. Pat. No. 3,476,821 to Brandenburg et al. discloses disproportionation reactions employing mordenite catalysts having silica/alumina ratios within the range of 10-100 and preferably within the range of about 20-60. The mordenites are modified by the inclusion of a sulfided metal selected from the Group VIII metals. Disclosed temperature range from about 400°-750° F.

Bhavikatti et al., "Toluene Disproportionation Over Aluminum-Deficient and Metal-Loaded Mordenites. 1. Catalytic Activity and Aging", Ind. Eng. Chem. Prod. Res. Dev. 1981, 20, 102-105, discloses toluene disproportionation at 400° C. over mordenite catalysts having silica/alumina mole ratios ranging from 12 to 61 at atmospheric pressure and a space velocity (WHSV) of 1. As the silica/alumina mole ratio is increased, catalyst activity is substantially decreased while aging quality is increased.

U.S. Pat. No. 3,562,345 to Mitsche discloses the use of molecular sieves such as mordenite catalysts in the disproportionation of toluene. The catalysts are characterized by a silica/alumina mole ratio from about 6 to about 12, pore openings of from about 3 to about 18 Angstroms and the oxidized or reduced state, particularly Group VIB and Group VIII metals including molybdenum, tungsten, chromium, iron, nickel, cobalt, platinum, palladium, ruthenium, rhodium, osmium and iridium. Mitsche discloses transalkylation at temperatures from about 200° C. to about 480° C. and gives specific examples of transalkylation of toluene at temperatures of 420° C. and 450° C.

U.S. Pat. No. 3,677, 973 to Mitsche et. al., discloses the use of mordenite catalysts composited with an alumina salt providing a silica/alumina mole ratio of about 10 to about 30 in the disproportionation of toluene. The reaction conditions proposed in this patent appear similar to those set forth in the aforementioned Mitsche '345 patent and, as in Mitsche '345, discloses incorporating Group VIB and Group VIII metals into the catalyst.

U.S. Pat. No. 4,151,120 to Marcilly discloses a process for the manufacture of a hydrocarbon conversion catalyst involving incorporating cobalt, nickel, silver or palladium in a mordenite catalyst having a silica/alumina mole ratio within the range of 10–100. Following incorporation of the metal into the mordenite, the catalyst is dried and subjected to a dry calcination procedure at a temperature within the range of 300°–700° C. in the presence of an inert or oxidizing gas having a moisture content of less than 1 percent. Marcilly '120 discloses various examples of the dismutation of toluene under reaction conditions 420° C., 30 bars, a space velocity (WHSV) of 5 and a hydrogen/hydrocarbon mole ratio of 5.

U.S. Pat. No. 4,723,048 to Dufresne et al. discloses a process for the dismutation of toluene employing a zeolite catalyst modified by the inclusion of metals. The catalyst is described as a sodium containing mordenite in the nature of so-called "wide pore" mordenite, i.e., mordenite with main pores, exhibiting a diameter of 7–10 Angstroms or "small pore" mordenite, mordenites with main pores exhibiting a diameter of 4–6 Angstroms. The mordenites are treated to extract sodium therefrom to provide not more than 1.0 percent by weight sodium ions and preferably not more than 0.5 percent by weight sodium ions. Dufresne discloses mordenites having silica/alumina ratios ranging from approximately 10 to 60, and modified by the inclusion of nickel and other metals. Dufresne '048 discloses activities of the nickel modified catalysts before and after an accelerated aging procedure at conversion rates of 10 percent and 45 percent.

The representative prior art discussed above reveals that much of the experimental and investigative work conducted in regard to alkylaromatic disproportionation employing metal promoted mordenite catalysts has been directed toward either achieving a higher level of alkylaromatic conversion or extending catalyst life (ie: controlling catalytic deactivation). Because it is believed to enhance reaction stability and catalyst aging character (both of which are advantageous due to the cost of the catalyst), it is generally known that it is desirable to employ a hydrogen cofeed in the disproportionation of alkylaromatics.

The amount of hydrogen supplied to the reaction zone is measured in terms of the hydrogen to toluene mole ratio. For example, the cited references of Marcilly '120, Butler '258 and Bhavikatti (described supra) generally teach hydrogen to toluene mole ratios greater than 3. The conventional use of a hydrogen cofeed is generally considered to prolong the useful life of the catalyst.

However, while the use of hydrogen as a cofeed can extend the life of the catalyst, an associated problem with using hydrogen at the start up of the disproportionation process is that, in the presence of the fresh catalyst, hydrogenation (which results when hydrogen is cofed with an alkylaromatic under disproportionation conditions) yields high concentrations of non-aromatic by-products in the disproportionation product. These non-aromatics, principally including methylcyclohexane and, to a lesser extent, other paraffinic and cyclic compounds, prevent optimum levels of the desired disproportionation products, i.e., benzene and xylene(s). Additionally, due to similar freezing points, it is very difficult to separate the produced benzene from the methylcyclohexane. Because of this difficulty in separation and the extensive hydrogenation activity, the selectivities to benzene and xylene(s) do not reach optimum levels until the by-production of non-aromatics decreases. While the formation of non-aromatics will naturally decrease (and stabilize) in direct relation to catalyst age, it would be desirable to shorten the period required to wait for such stabilization. Further, the selectivity to benzene and xylene(s) in toluene disproportionation is dependent upon the by-production level of non-aromatic compounds which, until stabilized, prevent optimum selectivity to the benzene and xylene(s).

Consequently, a long felt need continues to exist for an improved procedure for use in the disproportionation of alkylaromatics that results in greater selectivity to benzene (and xylene(s)), contemporaneous with an appreciable decrease in by-production of non-aromatic compounds such as methylcyclohexane, while not reducing catalyst life.

SUMMARY OF THE INVENTION

In accordance with the present invention, there is provided an improved process for the disproportionation of alkylaromatic feed stock which yields enhanced selectivities to benzene and xylene(s), contemporaneous with an appreciable decrease in associated non-aromatic by-products. Additionally, catalyst life is preserved. This process includes using an unconventionally low hydrogen to toluene mole ratio during reaction start-up, i.e., until the production of non-aromatics begins to stabilize; thereafter the ratio is increased. Reducing the hydrogen content at the beginning of the reaction substantially lessens any hydrogenation activity, thereby gaining optimum selectivities to benzene at a much sooner rate than that achieved using more conventional hydrogen to toluene ratios. The post start-up increase in hydrogen concentration following stabilized production of non-aromatics is generally believed to enhance the aging character of the catalyst, thereby preserving catalyst life.

In practicing the invention, a reaction zone is established by loading a metal-modified mordenite catalyst into the reaction zone. The reaction zone is operated under disproportionation conditions, including a temperature within the range of 250° C. to 450° C. and a pressure of at least 550 psig. A start-up procedure is initiated in which a toluene containing feed stock is continuously supplied to the reaction zone. Contemporaneous with the introduction of the toluene, hydrogen gas is introduced into the reaction zone to provide a hydrogen to toluene mole ratio of between 0.5 and 1.5. The feed stock contacts the catalyst forming a disproportionation product containing benzene, xylene(s) and non-aromatic by-products. The disproportionation product is continuously withdrawn and measured to determine its non-aromatic content. When the non-aromatic content of the disproportionation product is at a level not greater than approximately 1.0–1.3 weight percent in the product, it is an indication that the production of non-aromatic by-products has stabilized. Thereafter, the amount of hydrogen supplied to the reaction zone is increased as the process continues, to provide a hydrogen to toluene mole ratio in the range of 3 to 5.

The present invention confers several technical advantages over the prior art. One, as an aromatic solvent of comparatively high commercial value and virtually continuous demand, there exists sound economic rationale for increasing the efficiency of the means by which benzene and xylene(s) are produced. In addition, and with respect to refining operation, the distillation separation of benzene from non-aromatic compounds having a comparable freezing point range, such as methylcyclohexane, is markedly enhanced due to the significant decrease in non-aromatic by-production, which is an object of the instant invention. Third, by adjusting the amount of hydrogen supplied to the reaction zone at different stages throughout the procedure, catalyst life is preserved. Fourth, the procedure is relatively burden-free and can be accomplished without incurring significant additional cost.

BRIEF DESCRIPTION OF THE DRAWINGS

Further aspects of the invention and their advantages may be discerned when one refers to the following detailed description as taken in conjunction with the drawings, in which:

FIGS. 3 and 4 are graphs illustrating product selectivity to non-aromatics and benzene as a function of catalyst age in conjunction with a toluene disproportionation process carried out over a nickel-modified mordenite catalyst wherein hydrogen is supplied to the reaction zone at gradually increasing rates.

DESCRIPTION OF THE PREFERRED EMBODIMENTS

Figure 1:
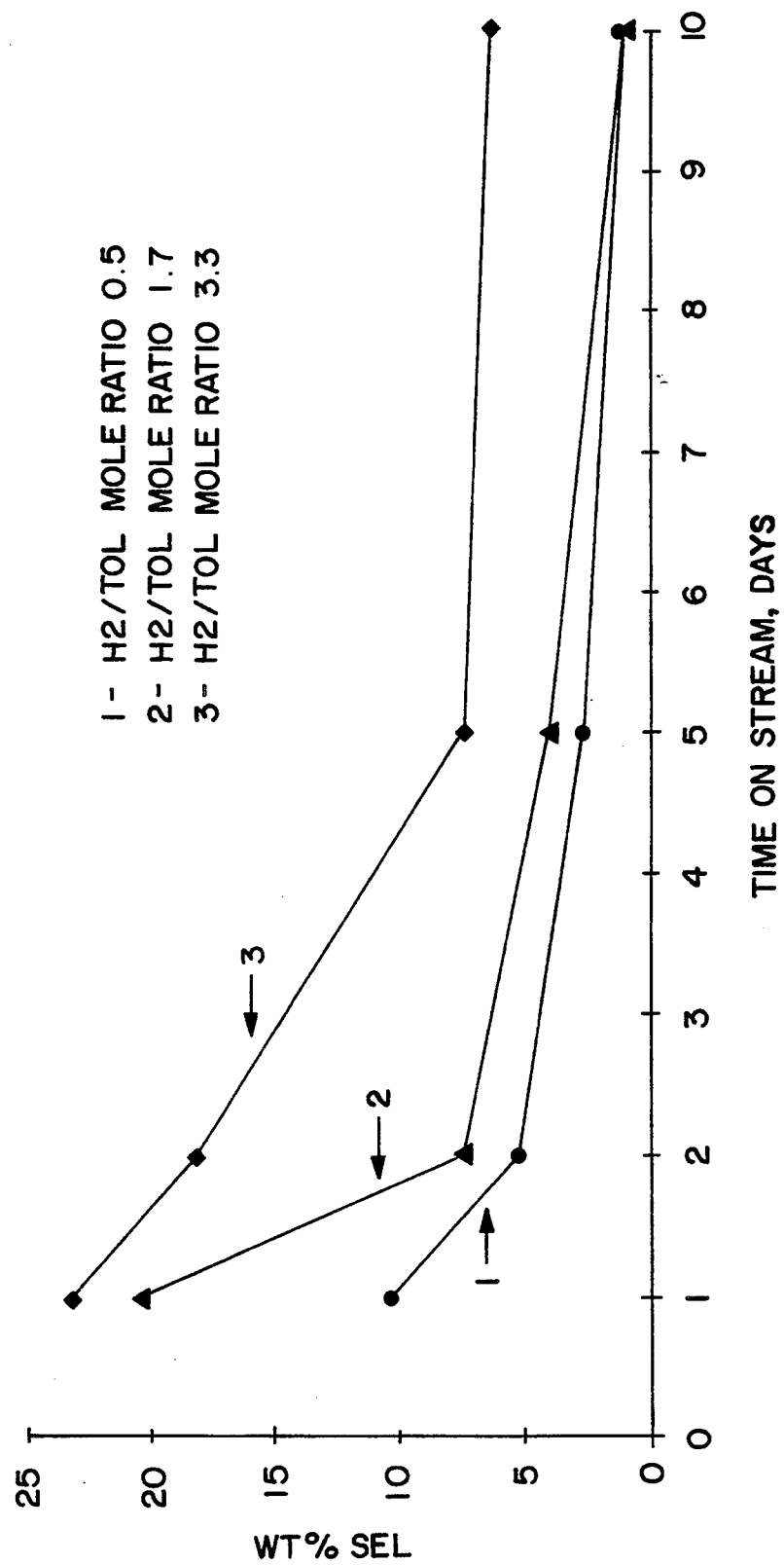
FIG. 1 is a graph illustrating product selectivity to non-aromatic compounds as a function of catalyst age in conjunction with a toluene disproportionation process carried out over a nickel-modified mordenite catalyst wherein hydrogen is co-fed with toluene in molar relationships of 0.5, 1.7 and 3.3.

As evidenced in the foregoing discussion, the use of hydrogen in the disproportionation of toluene over a metal modified zeolite catalyst is well known in the art. In the present invention, however, the amount of hydrogen supplied to the reaction zone is critically adjusted during the toluene disproportionation process providing an increase in selectivities to benzene and xylene(s), contemporaneous with a decrease in selectivities to associated non-aromatic by-products.

In accordance with the invention, the toluene disproportionation process begins with a start up procedure in which a toluene containing feed stock is supplied to a reaction zone containing a metal promoted mordenite catalyst. The reaction zone is operated under disproportionation conditions including a temperature within the range of 250° C. to 450° C. and a pressure of at least 550 psig. Contemporaneous with the toluene, hydrogen gas is co-fed into the reaction zone, at a rate sufficient to provide a hydrogen to toluene molar ratio of between about 0.5 and 1.5. The feed stock contacts the catalyst forming a disproportionation product containing benzene, xylene(s) and non-aromatic by-products. The disproportionation product is continuously withdrawn and measured to determine its non-aromatic content. When the non-aromatic content of the disproportionation product is at a level not greater than approximately 1.0 weight percent in the product, it is an indication that the production of non-aromatic by-products has stabilized, At the end of the start-up process, i.e., when the level of non-aromatics is not greater than approximately 1.0 weight percent in the products, the amount of hydrogen supplied to the reaction zone may be increased to provide a hydrogen to toluene mole ratio in the range of 3 to 5. Preferably, the amount of hydrogen supplied to the reactor zone is increased incrementally. For example, the hydrogen to hydrocarbon ratio may be raised from 1.0 to 2 or 2.5 and then from 2.5 to 3 and then maybe to 4. The disproportionation process continues, as one maintains careful observation that selectivities to non-aromatics remains stable, while withdrawing the product containing benzene and xylene(s) from the reaction zone.

The mordenite catalyst employed in the present invention preferably exhibits a silica to alumina molar ratio of between 16:1 and 22:1 and more preferably about 18:1. Additionally, the mordenite catalyst is modified by the inclusion of nickel. Applicants' experimentation suggests that the best results are obtained by utilizing a catalyst made up of no less than 1.0 weight percent nickel. While it is generally known in the art that low nickel content mordenite catalysts are useful in converting toluene and assist in selectivity to benzene and xylene(s), they have generally demonstrated poor aging quality (i.e., short catalyst life). Experimentation has demonstrated that, while greater amounts of nickel can be employed without corresponding significant benefit, one preferred upper limit of nickel content in the catalyst is about 1.5 weight per cent.

According to the present invention utilizing a nickel promoted mordenite catalyst, a toluene conversion level of about 48% can be achieved with minimal formation of non-aromatic compounds in the product stream by reducing the concentration of hydrogen co-feed during reaction start-up. This measure results in a higher yield of desirable benzene product. Although the precise point of optimum hydrogen to toluene ratio during start-up was not determined, it was determined that the most significant improvements are achieved between about 0.5–2.5 and, more preferably, between about 1.0–2.0. Once the level of non-aromatics measured in the disproportionation product stabilizes, the hydrogen to toluene mole ratio can be increased to within the range of 3 to 5, thereby preserving catalyst life.

FIGS. 1–4 graphically characterize the distinct advantages of the present invention. In conjunction with FIGS. 1 and 2, the following Table I is provided, which describes the data used to generate lines 1–6 on FIGS. 1 and 2.

TABLE I

Effect of hydrogen in toluene feed on product distribution during first 10 days of run.

| | Catalyst Age (Days) | H₂/Toluene Molar Ratio | | |
|---|---|---|---|---|
| | | 0.5 | 1.7 | 3.3 |
| Selectivity (Wt %) | | | | |
| Non-aromatics | 1 | 10.34 | 20.46 | 23.15 |
| | 2 | 5.27 | 7.45 | 18.16 |
| | 5 | 2.70 | 4.05 | 7.47 |
| | 10 | 1.15 | 1.12 | 6.37 |
| Benzene | 1 | 31.68 | 26.55 | 10.98 |
| | 2 | 35.48 | 33.74 | 20.12 |
| | 5 | 38.76 | 41.56 | 22.79 |
| | 10 | 41.07 | 41.56 | 30.94 |
| Xylene(s) | 1 | 41.51 | 36.16 | 32.25 |
| | 2 | 43.31 | 40.05 | 40.55 |
| | 5 | 45.18 | 44.31 | 47.36 |
| | 10 | 45.57 | 46.72 | 43.29 |
| Heavies | 1 | 12.14 | 12.85 | 13.74 |
| | 2 | 12.30 | 10.69 | 13.59 |
| | 5 | 10.52 | 10.19 | 10.54 |
| | 10 | 9.69 | 9.30 | 9.78 |

FIG. 1 graphically illustrates the rapid drop in selectivity to non-aromatic by-products as a function of catalyst age. Line 1 represents the selectivity during the first ten days when a hydrogen to toluene mole ratio of 0.5 is used. As can be seen from the figure, after five days, product selectivity to non-aromatic by-products was just 2.7 weight percent. Line 2 represents the selectivity during the first ten days when a hydrogen to toluene mole ratio of 1.7 is used. As can be seen from the figure, after just five days, selectivity to non-aromatic by-products was approximately 4 weight percent. After ten days, selectivities to non-aromatics dropped to approximately 1 weight percent for hydrogen to toluene ratios of 0.5 and 1.7. Line 3 represents the selectivity during the first ten days when a hydrogen to toluene mole ratio of 3.3 is used. After ten days, at this higher, yet more conventional ratio, the selectivity to non-aromatics had only dropped to between 6 and 7 weight percent.

Figure 2:
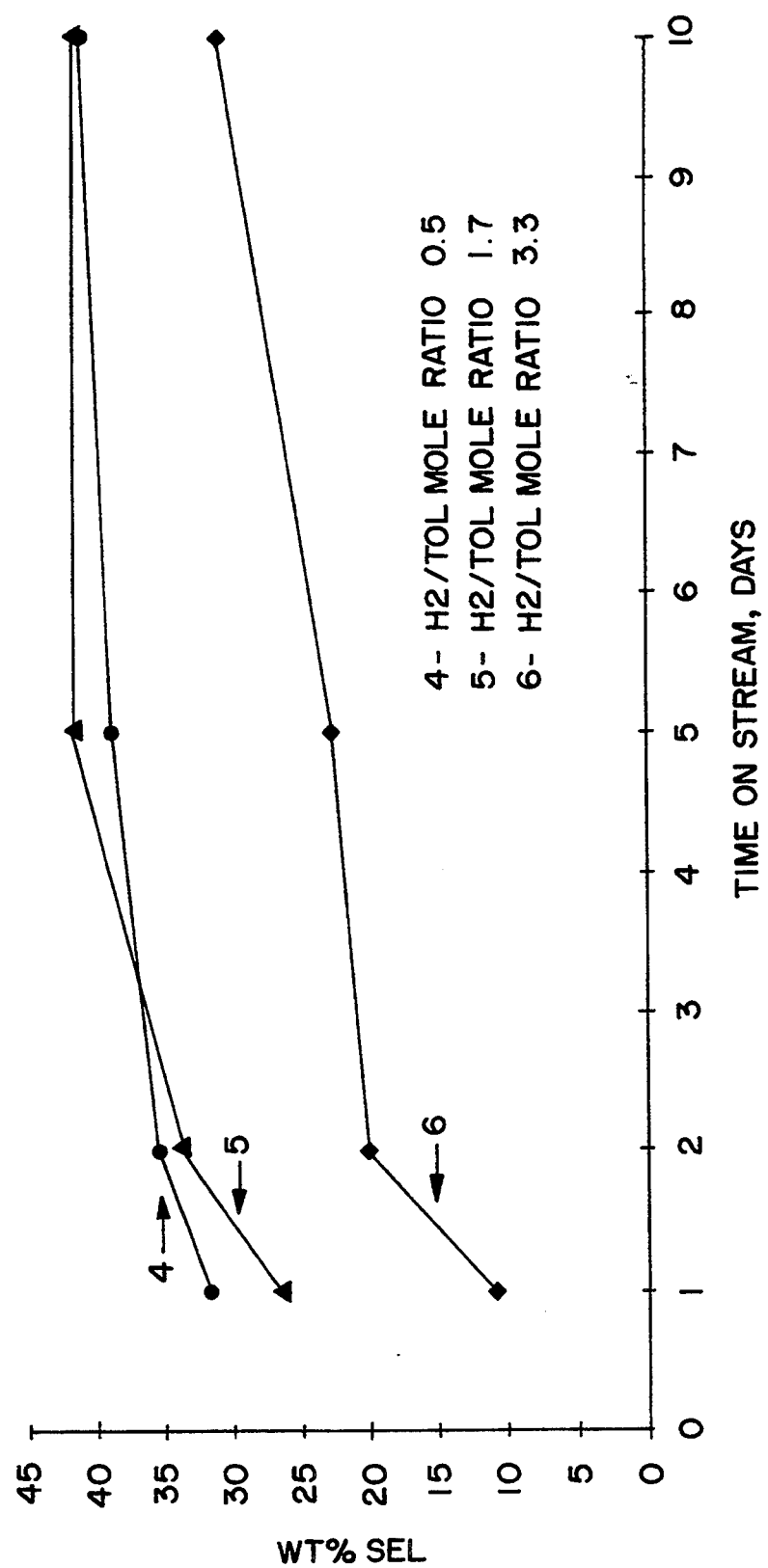
FIG. 2 is a graph illustrating product selectivity to benzene as a function of catalyst age in conjunction with a toluene disproportionation process carried out over a nickel-modified mordenite catalyst wherein hydrogen is co-fed with toluene in molar relationships of 0.5, 1.7 and 3.3.

FIG. 2 graphically illustrates the marked rise in selectivity to benzene as a function of catalyst age. Line 4 represents the selectivity during the first 10 days when a hydrogen to toluene mole ratio of 0.5 is used. As can be seen from FIG. 2, after 5 days, selectivity to benzene was almost 40 weight percent. Line 5 represents the selectivity during the first 10 days when a hydrogen to toluene mole ratio of 1.7 is used. As can be seen from the figure, after 5 days selectivity to benzene is just over 40 weight percent and had stabilized at that point. Line 6 represents the selectivity during the first 10 days when a hydrogen to toluene mole ratio of 3.3 is used. After 10 days at this more conventional mole ratio, the selectivity to benzene was only about 31 weight percent. This low selectivity illustrated by line 6, is directly attributable to the high level of non-aromatics, i.e., above 6 weight percent (illustrated by line 3 in FIG. 1), still in the disproportionation product stream. Using this more conventional mole ratio of 3–4, the formation of non-aromatics does not decrease to the desired level of about 1 weight percent until the end of approximately 30 days (not shown).

As described in accordance with the present invention, after the level of non-aromatics present in the disproportionation product decreases and stabilizes, the amount of hydrogen supplied to the reaction zone should be increased in order to preserve the catalyst life. Preferably the hydrogen is increased in incremental steps as it is introduced into the reaction zone. For example, once the selectivity to non-aromatics in the disproportionation product is at a level not greater than 1 weight percent in the products, the amount of hydrogen supplied to the reaction zone could be increased to provide a hydrogen to toluene mole ratio of 2. This mole ratio could be maintained for a few days and then the hydrogen supplied to the reaction zone could be increased to provide a mole ratio of approximately 3. This incremental process is then continued until the hydrogen to toluene ratio is between 3 and 5, while maintaining careful observation that the non-aromatic level remains stable.

FIGS. 3 and 4 graphically illustrate the selectivities to non-aromatics and benzene as a function of catalyst age as the start-up process concludes and the hydrogen to toluene mole ratio is increased according to the invention. As can be observed in each of these figures, once the non-aromatic by-production has stabilized, raising the hydrogen to toluene ratio does not compromise the selectivities to benzene. As shown in FIG. 3, during start-up, the hydrogen to toluene mole ratio was approximately 1.1, illustrated at Point A. After stabilization, the hydrogen to toluene mole ratio was raised from 1.1 to 2.5, illustrated at Point B. Finally, the hydrogen to toluene mole ratio was raised from 2.5 to 4.5 with no marked change in selectivities, illustrated at Point C. FIG. 4 depicts a start-up process where the initial hydrogen to toluene mole ratio was approximately 1, shown at Point D. Point E illustrates that no change occurred when the hydrogen to toluene mole ratio was raised from 1 to 2. Finally, Point F illustrates that no marked change occurred when the hydrogen to toluene ratio was increased from 2 to 3.

One can observe that the low hydrogen to toluene mole ratio used during the start-up process enhances selectivity to benzene and xylene(s), thus increasing the economic efficiencies of the toluene disproportionation process. Additionally, catalyst life is preserved in conjunction with the critical staged adjustment of the amount of hydrogen supplied to the reaction zone. This novel procedure provides a significant improvement over the prior art without incurring significant additional cost.

The present invention resulted from a study conducted using different hydrogen to toluene mole ratios in a laboratory reactor. In each case, the catalyst was pre-dried by heating at a suitable temperature, preferably 250° C., under the flow of hydrogen gas. Thereafter, a substantially pure toluene feedstock was introduced into the reaction zone at a liquid hourly space velocity (LHSV) of approximately 2 hr$^{-1}$. The reaction zone was operated at a starting temperature of 250° C., which was subsequently raised incrementally to within the range of about 320° C.–330° C., and at a pressure of approximately 600 psig. During the start-up procedure and once the level of non-aromatics in the product stream decreased and stabilized, the reactor temperature was incrementally increased in an effort to maintain the desired 48% conversion. It was found that the catalyst used herein stabilized (i.e., a desirable level of toluene conversion is maintained at 46–48% without marked temperature increases) at approximately 420° C.

While the invention has been described with reference to particular embodiments thereof, it would be apparent to those skilled in the art that various changes and modifications can be made without departing from the spirit of the invention or from the scope of the appended claims.

What is claimed is:

1. A process for disproportionating a toluene-containing feed stock to produce a disproportionation product containing benzene and xylene which comprises:
   (a) initiating a start-up procedure comprising:
      (1) establishing a reaction zone by loading into said reaction zone a nickel-modified mordenite catalyst, said reaction zone being maintained under disproportionation conditions, including a temperature within the range of 250° C. to 450° C. and a pressure of at least 550 psig;
      (2) passing said toluene feed stock into said reaction zone and into contact with said catalyst;
      (3) supplying hydrogen gas into said reaction zone at a rate to provide a hydrogen to toluene mole ratio of between 0.5 and 1.5;
      (4) continuously withdrawing said disproportionation product containing benzene and xylene and measuring non-aromatic levels in said product;
      (5) further continuing to pass said toluene feed stock and hydrogen into said reaction zone until said disproportionation product contains levels of nonaromatics not greater than about 1.0 to 1.3 weight percent;
   (b) thereafter continuing to pass said toluene feed stock and hydrogen into said reaction zone, incrementally increasing amount of said hydrogen to provide a hydrogen to toluene mole ratio of between 3 and 5; and
   (c) withdrawing said disproportionation product from said reaction zone.

2. The process according to claim 1, wherein during said start-up procedure, said hydrogen to toluene mole ratio is approximately 1.0.

3. The process according to claim 1, wherein during step (b) the hydrogen to toluene mole ratio is raised in increments of 1.0 to 1.5 until said hydrogen to toluene mole ratio is between 4 and 5.

4. The process according to claim 1, wherein said disproportionation product contains non-aromatics comprising methylcyclohexane.

5. The process according to claim 1, wherein said disproportionation product exhibits selectivity to non-aromatics of not greater than about 1.1 weight percent in the product.

6. The process according to claim 1, wherein said disproportionation product exhibits selectivity to benzene of not less than about 40 weight percent.

7. The process according to claim 1, wherein during step (a) said disproportionation product exhibits selectivity to benzene of not less than about 40 weight percent in the product in at least the first ten days of said process.

8. The process according to claim 1, wherein said disproportionation product exhibits selectivity to xylene of not less than approximately 45 weight percent.

9. The process according to claim 1, wherein during step (a) said disproportionation product exhibits selectivity to non-aromatics of not greater than 1.3 weight percent in the product in at least the first ten days of said process.

10. The process according to claim 1, wherein said toluene conversion rate is at least 46%.

11. The process according to claim 1, wherein said catalyst exhibits a silica to alumina mole ratio within the range of 16:1 to 22:1.

12. The process according to claim 1, wherein said catalyst exhibits a nickel concentration within the range of 1.0 to 1.5 weight percent.

* * * * *